(12) United States Patent
Despres, III et al.

(10) Patent No.: US 7,125,193 B2
(45) Date of Patent: Oct. 24, 2006

(54) MODULAR CONNECTION FOR ORTHOPEDIC COMPONENT

(75) Inventors: Alfred S. Despres, III, Shingle Springs, CA (US); Daniel E. E. Hayes, Jr., Placerville, CA (US)

(73) Assignee: Depuy Products, Inc., Warsaw, IN (US)

( * ) Notice: Subject to any disclaimer, the term of this patent is extended or adjusted under 35 U.S.C. 154(b) by 35 days.

(21) Appl. No.: 10/749,136

(22) Filed: Dec. 30, 2003

(65) Prior Publication Data

US 2005/0089365 A1 Apr. 28, 2005

Related U.S. Application Data

(63) Continuation of application No. 09/909,929, filed on Jul. 20, 2001, now Pat. No. 6,669,728.

(60) Provisional application No. 60/219,963, filed on Jul. 20, 2000, provisional application No. 60/219,955, filed on Jul. 20, 2000.

(51) Int. Cl.
*F16B 7/00* (2006.01)

(52) U.S. Cl. ............... 403/297; 403/277; 403/280; 403/292; 403/334; 623/18.11

(58) Field of Classification Search ........ 403/277, 403/280, 285, 292, 294, 297, 333, 334; 623/18.11
See application file for complete search history.

(56) References Cited

U.S. PATENT DOCUMENTS

| 3,848,272 A | 11/1974 | Noiles |
| RE28,895 E | 7/1976 | Noiles |
| 4,355,429 A | 10/1982 | Mittelmeier et al. |
| 4,520,511 A * | 6/1985 | Gianezio et al. ......... 623/22.46 |
| 4,790,852 A | 12/1988 | Noiles |
| 4,846,839 A | 7/1989 | Noiles |
| 4,851,007 A | 7/1989 | Gray |
| 4,878,917 A * | 11/1989 | Kranz et al. ............. 623/23.45 |
| 4,936,853 A | 6/1990 | Fabian et al. |
| 5,080,685 A | 1/1992 | Bolesky et al. |
| 5,108,452 A | 4/1992 | DeMane et al. |
| 5,156,624 A | 10/1992 | Barnes |
| 5,181,928 A | 1/1993 | Bolesky et al. |
| 5,286,260 A | 2/1994 | Bolesky et al. |
| 5,370,706 A | 12/1994 | Bolesky et al. |
| 5,507,830 A | 4/1996 | DeMane et al. |
| 5,540,694 A | 7/1996 | DeCarlo, Jr. et al. |
| 5,725,592 A | 3/1998 | White et al. |
| 5,766,255 A | 6/1998 | Slamin et al. |
| 5,782,921 A | 7/1998 | Colleran et al. |
| 5,876,459 A | 3/1999 | Powell |
| 5,902,340 A | 5/1999 | White et al. |
| 5,906,644 A | 5/1999 | Powell |
| 6,102,956 A | 8/2000 | Kranz |
| 6,139,584 A * | 10/2000 | Ochoa et al. ............. 623/23.46 |
| 6,264,699 B1 * | 7/2001 | Noiles et al. ............. 623/23.23 |
| 6,299,648 B1 | 10/2001 | Doubler et al. |
| 6,319,286 B1 | 11/2001 | Fernandez et al. |
| 6,355,069 B1 * | 3/2002 | DeCarlo et al. ......... 623/23.26 |
| 6,669,728 B1 * | 12/2003 | Despres et al. .......... 623/16.11 |

* cited by examiner

*Primary Examiner*—Daniel P. Stodola
*Assistant Examiner*—Michael P. Ferguson
(74) *Attorney, Agent, or Firm*—Pandiscio & Pandiscio

(57) ABSTRACT

An orthopedic component comprising a first element and a second element, with the first element and the second element being secured to one another with a modular connection, wherein the modular connection comprises a taper junction and an engaged-fit junction.

5 Claims, 5 Drawing Sheets

MODULAR CONNECTION FOR ORTHOPEDIC COMPONENT

REFERENCE TO PENDING PRIOR PATENT APPLICATIONS

This is a continuation of prior U.S. patent application Ser. No. 09/909,929, filed Jul. 20, 2001 now U.S. Pat. No. 6,669,728 by Alfred S. Despres III et al. for MODULAR CONNECTION FOR ORTHOPEDIC COMPONENT, which in turn claims benefit of prior U.S. Provisional Patent Application Ser. No. 60/219,955, filed Jul. 20, 2000 by Alfred S. Despres III et al. for MODULAR ORTHOPEDIC CONNECTION; and prior U.S. Provisional Patent Application Ser. No. 60/219,963, filed Jul. 20, 2000 by Alfred S. Despres III et al. for FORCE COUPLE CONNECTION.

FIELD OF THE INVENTION

This invention relates to surgical apparatus and procedures in general, and more particularly to orthopedic components.

BACKGROUND OF THE INVENTION

Orthopedic components are well known in the art.

For example, in joint replacement surgery, portions of a joint are replaced with orthopedic components so as to provide long-lasting function and pain-free mobility. More particularly, in the case of a prosthetic total hip joint, the head of the femur is replaced with a prosthetic femoral stem component, and the socket of the acetabulum is replaced by a prosthetic acetabular cup component, whereby to provide a prosthetic total hip joint. Similarly, in the case of a prosthetic total knee joint, the top of the tibia is replaced by a prosthetic tibial component, and the bottom of the femur is replaced by a prosthetic femoral component, whereby to provide a prosthetic total knee joint.

Orthopedic components are also used in a variety of other ways. For example, orthopedic components may be used to stabilize a fractured bone, or to secure two vertebral bodies together, or to hold a bone graft to a bone, or to secure soft tissue to a bone, etc.

In many situations, an orthopedic component may comprise two or more elements which may need to be secured to one another. By way of example, in the case of a prosthetic total hip joint, the prosthetic femoral stem component is sometimes constructed out of a plurality of separate elements, wherein each of the elements may be independently selected so as to most closely approximate patient anatomy, and wherein the separate elements may be assembled to one another using modular connections, so as to provide the best possible prosthetic femoral stem component for the patient. Similarly, in the case of a prosthetic total knee joint, the prosthetic tibial component is also sometimes formed out of a plurality of separate elements which are assembled using modular connections. Still other types of orthopedic components may require, or may benefit from, the assembly of a plurality of separate elements using modular connections.

Once deployed in the patient's body, the orthopedic components, and hence the modular connections securing the separate elements to one another, are typically subjected to axial, bending and torsional loads. While different types of modular connections are known in the art, no one type of existing modular connection is ideal for dealing with all three types of loads, i.e., axial, bending and torsional loads.

By way of example, taper connections generally accommodate axial (i.e., compressive) loads well, but they generally do not accommodate bending and torsional loads particularly well. By way of further example, concentric cylinder connections generally accommodate bending loads well, but they generally do not accommodate axial and torsional loads particularly well.

SUMMARY OF THE INVENTION

As a result, one object of the present invention is to provide an improved modular connection for connecting together a plurality of separate elements so as to form an orthopedic component.

Another object of the present invention is to provide an improved orthopedic component.

These and other objects are addressed by the provision and use of the present invention.

In one form of the invention, there is provided an improved modular connection for connecting together a plurality of separate elements so as to form an orthopedic component, the improved modular connection comprising, in combination, a taper junction and an engaged-fit junction.

In another form of the invention, there is provided an improved orthopedic component comprising a first element and a second element, with the first element and the second element being secured to one another with a modular connection, wherein the modular connection comprises, in combination, a taper junction and an engaged-fit junction.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts and further wherein.

DETAILED DESCRIPTION OF THE PREFERRED EMBODIMENTS

Figure 1:
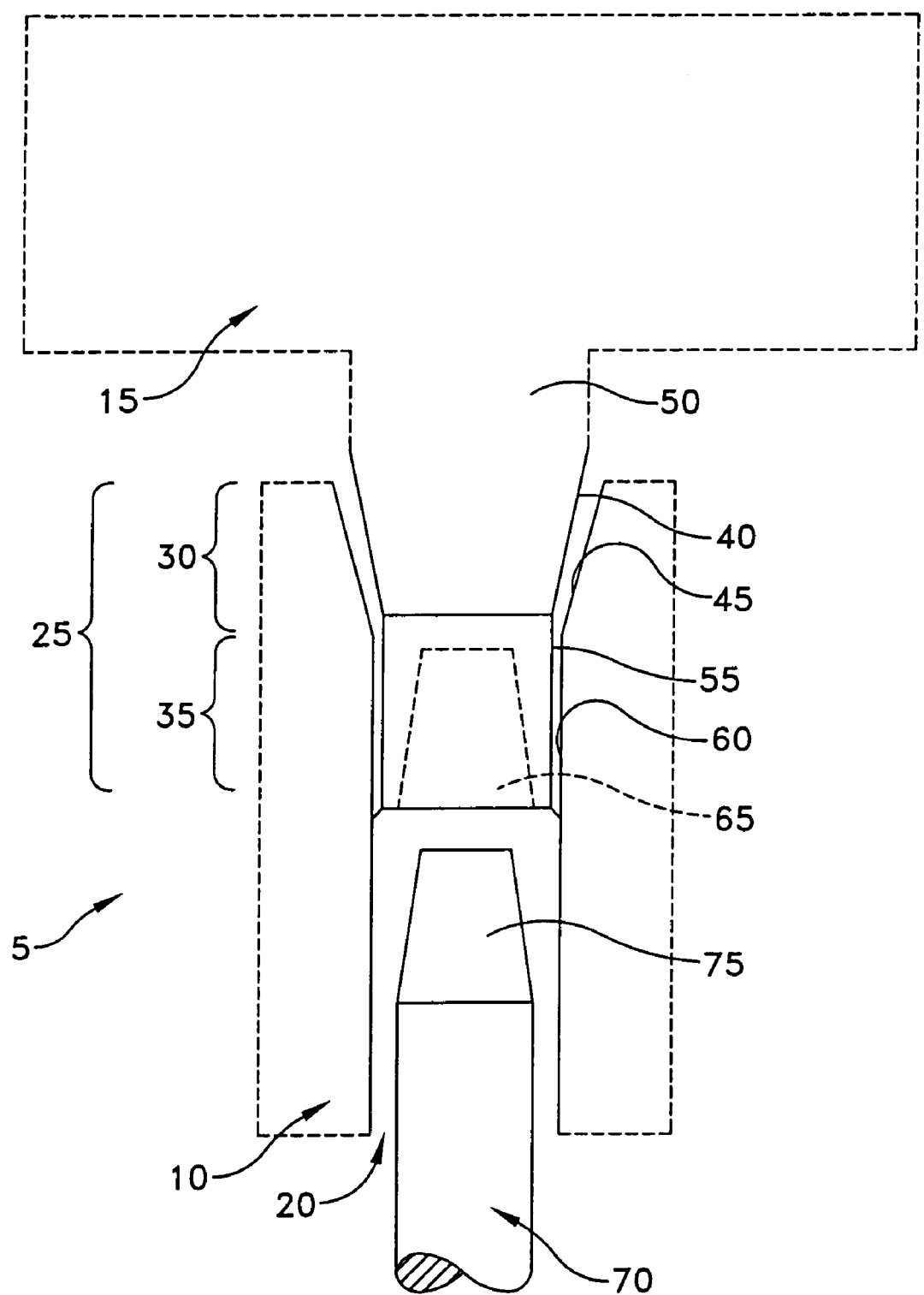
FIG. 1 is a schematic, exploded side view of one form of modular connection formed in accordance with the present invention.

Looking first at FIG. 1, there is shown an orthopedic component 5 formed in accordance with the present invention. Orthopedic component 5 may comprise a prosthetic femoral stem component of the sort used in a prosthetic total hip joint and comprising a plurality of separate elements which are assembled using a modular connection; or orthopedic component 5 may comprise a prosthetic tibial component of the sort used in a prosthetic total knee joint and comprising a plurality of separate elements which are assembled using a modular connection; or orthopedic component 5 may comprise any other type of orthopedic component which may require, or which may benefit from, the assembly of a plurality of separate elements using a modular connection.

Orthopedic component 5 generally comprises a first element 10 and a second element 15. First element 10 includes an aperture 20 into which portions of second element 15 extend.

In accordance with the present invention, first element 10 and second element 15 are adapted to be secured to one another using an improved modular connection 25 so as to form the complete orthopedic component 5.

More particularly, modular connection 25 comprises, in combination, two load-bearing junctions: a taper junction 30 and an engaged-fit junction 35.

Taper taper junction 30 is formed by the interaction of a first taper 40 with a corresponding second taper 45. More particulary, first taper 40 is formed on a projection 50 of second element 15. Second taper 45 is formed along a portion of the sidewall defining the first body element's aperture 20. First taper 40 and second taper 45 seat securely against one another so as to together form the load-bearing taper junction 30.

The engaged-fit junction 35 is formed by the interaction of a first concentric wall 55 with a second concentric wall 60. More particularly, first concentric wall 55 is formed on projection 50 of second element 15. Preferably first concentric wall 55 is disposed on projection 50 coaxial with, and distal to, first taper 40. Second concentric wall 60 is formed along a portion of the sidewall defining the first element's aperture 20. Preferably second concentric wall 60 is disposed on first element 10 coaxial with, and distal to, second taper 45. First concentric wall 55 and second concentric wall 60 seat securely against one another so as to form the load-bearing engaged-fit junction 35.

In general, the engaged-fit junction 35 is a mechanical connection that achieves stability by the deformation of one member so that it is pressure locked against a constraining second member. This deformation can be expansion (e.g., as in a taper expanded collet) or contraction (e.g., as in a force fit). The deformation can also be effected by thermal expansion or thermal contraction (e.g., as with a shape memory alloy such as Nitinol or the like). Regardless of how the deformation is achieved, the resulting mechanical connection has surfaces which are forcefully engaged against one another as a result of the deformation, whereby to establish the engaged-fit junction.

As noted above, there are a number of ways in which first concentric wall 55 and second concentric wall 60 can be made to seat securely against one another so as to form the load-bearing engaged-fit junction 35.

For example, first concentric wall 55 can be made slightly oversized relative to second concentric wall 60, such that force fitting first concentric wall 55 internal to second concentric wall 60 will create the engaged-fit junction 35.

Alternatively, and in accordance with a preferred form of the present invention, the distal end of the second element's projection 50 may be formed with a recess 65, and the proximal end of third element 70 may include a projection 75 for insertion into recess 65. More particularly, projection 75 is oversized relative to recess 65, such that insertion of projection 75 into recess 65 will cause a radial expansion of first concentric wall 55 into engagement with second concentric wall 60, whereby to create the engaged-fit junction 35. In one preferred form of the invention, recess 65 and projection 75 are both tapered, and the distal end of second element 15 is a split collet. Alternatively, the distal end of second element 15 may be formed out of a material sufficiently resilient to engage second concentric wall 60 without being split.

Due to the unique construction of modular connection 25, orthopedic component 5 is able to accommodate axial, bending and torsional loads better than prior art devices. More particularly, modular connection 25 simultaneously provides two load-bearing junctions: the taper junction 30 and the engaged-fit junction 35. The taper junction 30 accommodates axial (i.e., compressive) loads extremely well. At the same time, the engaged-fit junction 35 accommodates bending and torsional loads extremely well. Additionally, the engaged-fit junction 35 stabilizes the taper junction 30 against bending and torsional loads. Together, the two load-bearing junctions collectively handle axial, bending and torsional loads significantly better than prior art devices.

Figure 2:
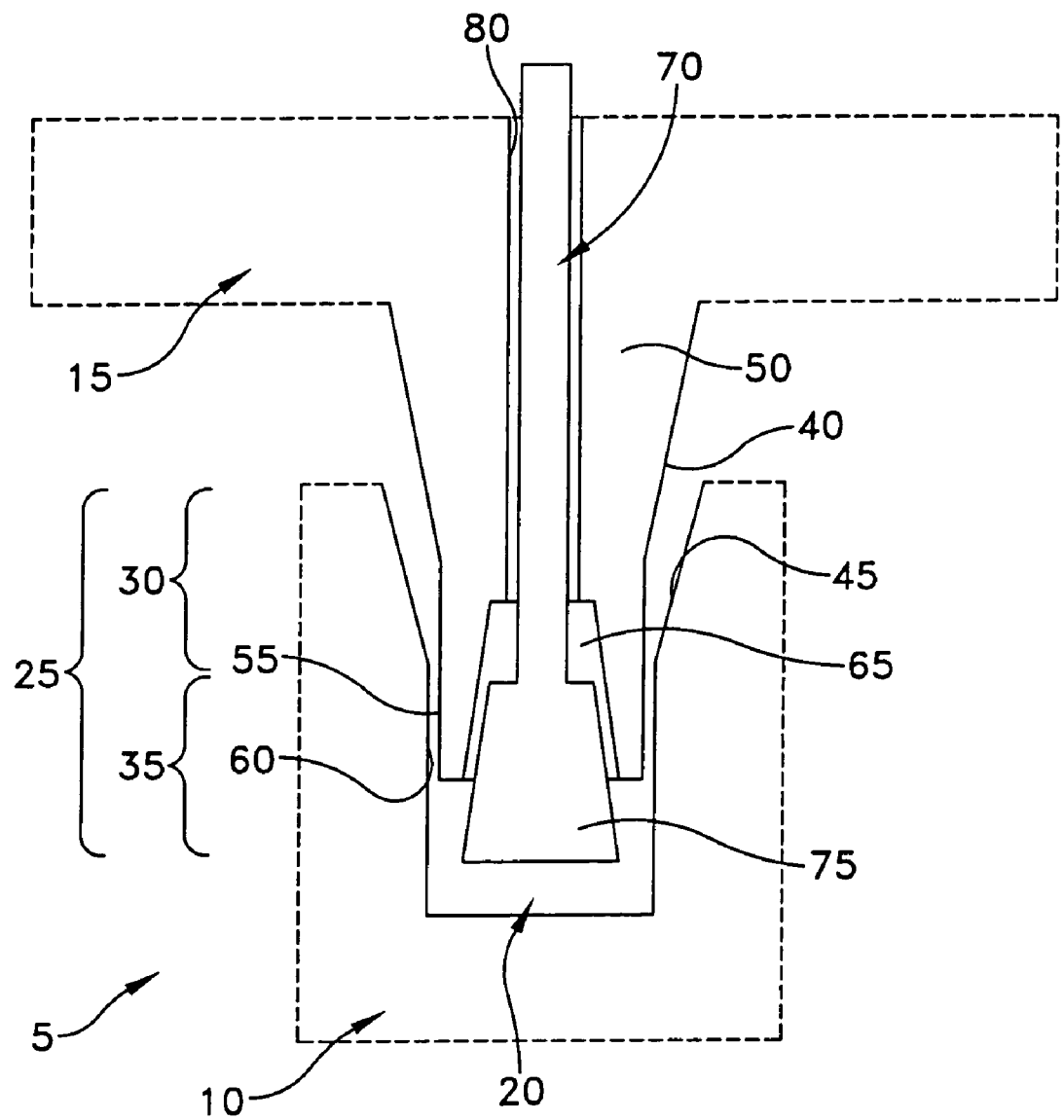
FIG. 2 is a schematic, exploded side view of another form of modular connection formed in accordance with the present invention.

Looking next at FIG. 2, there is shown an alternative form of construction. Here, the aperture 20 comprises a blind hole formed in first element 10, and third element 70 extends through an opening 80 formed in second element 15 and communicating with recess 65, with engaged-fit junction 35 being actuated by pulling proximally on third element 70 once first taper 40 has been seated against second taper 45.

Figure 3:
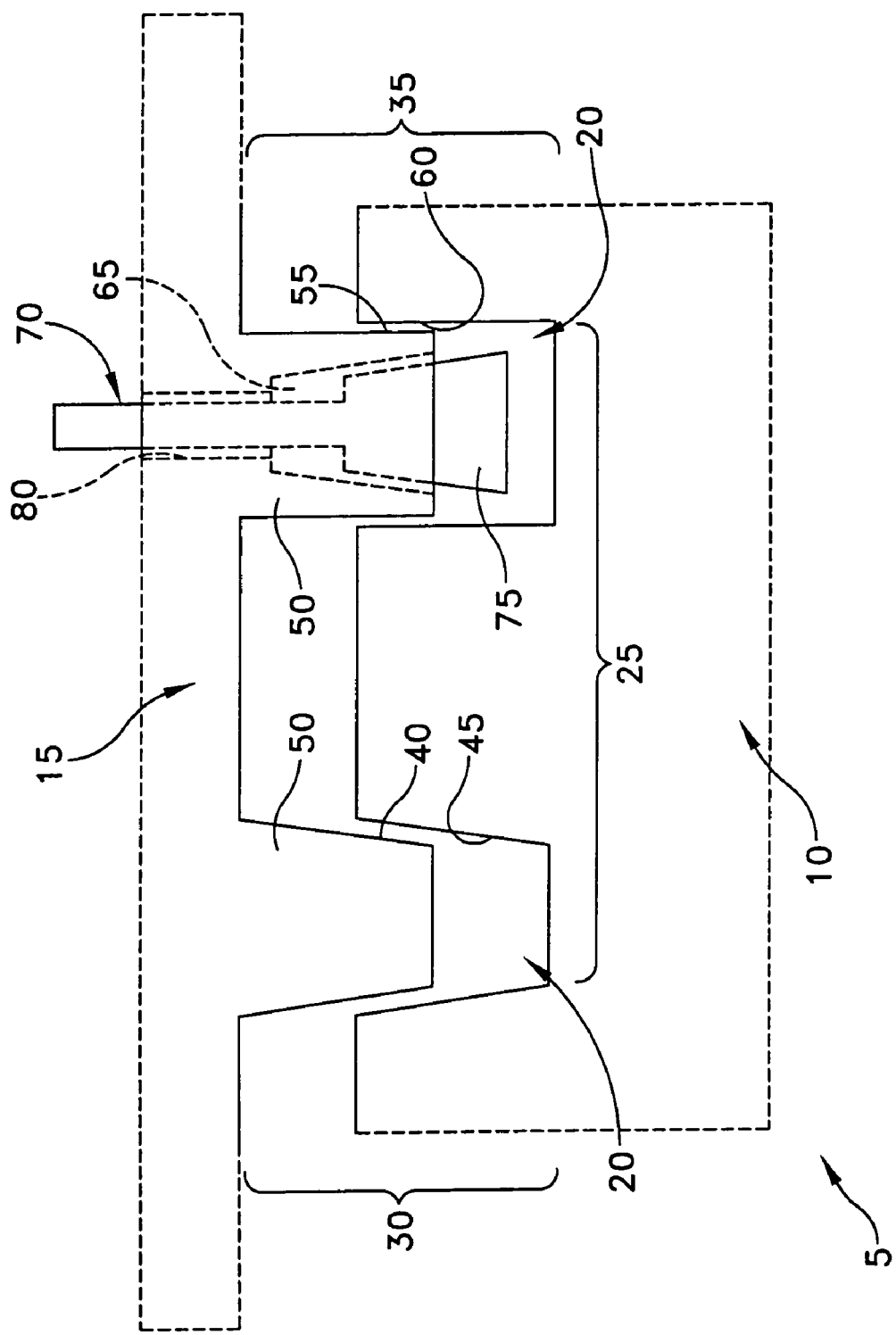
FIG. 3 is a schematic, exploded side view of still another form of modular connection formed in accordance with the present invention.

Looking next at FIG. 3, there is shown another alternative form of construction. Here, the taper junction 30 and the engaged-fit junction 35 are disposed parallel to one another, rather than coaxial with one another as shown in FIGS. 1 and 2. To this end, aperture 20 comprises a pair of parallel apertures 20, and projection 50 comprises a pair of parallel projections 50.

Figure 4:
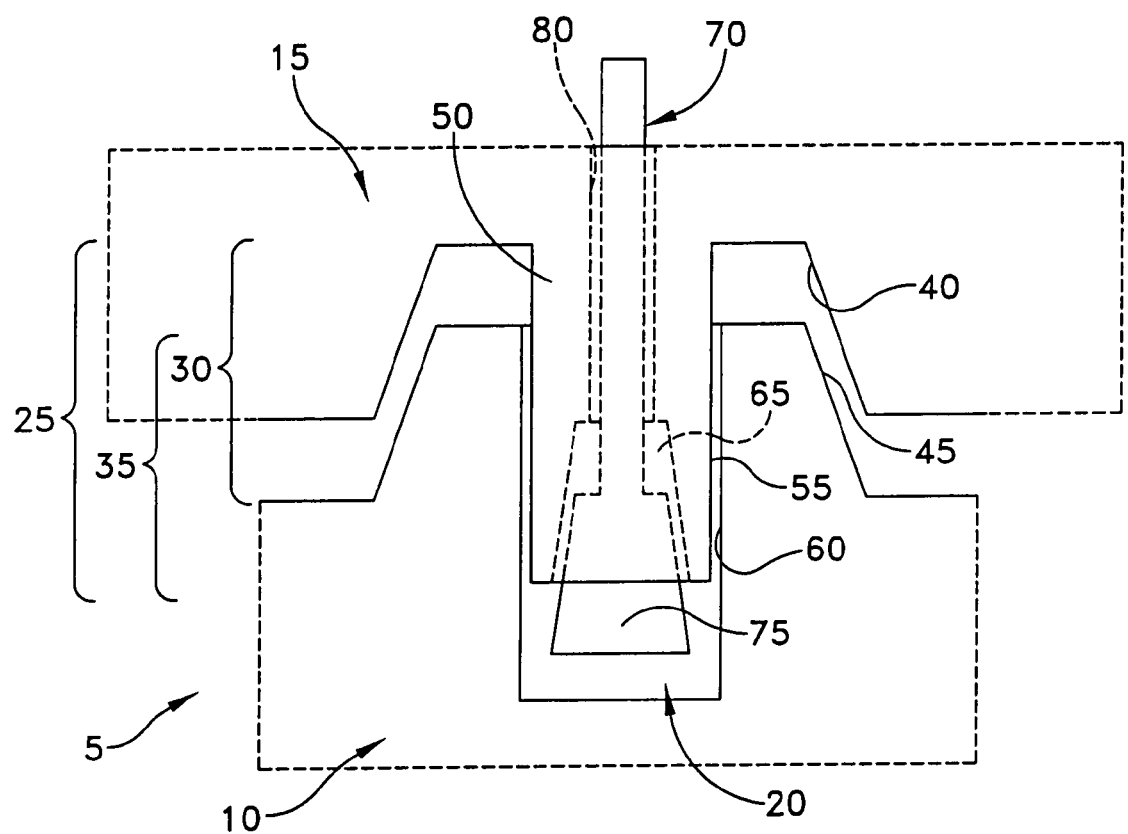
FIG. 4 is a schematic, exploded side view of yet another form of modular connection formed in accordance with the present invention.

Looking next at FIG. 4, there is shown still another alternative form of construction. Here, the taper junction 30 and the engaged-fit junction 35 are disposed coaxial and to at least some extent overlap with one another, rather than being axially separated in the manner shown in FIG. 2.

Figure 5:
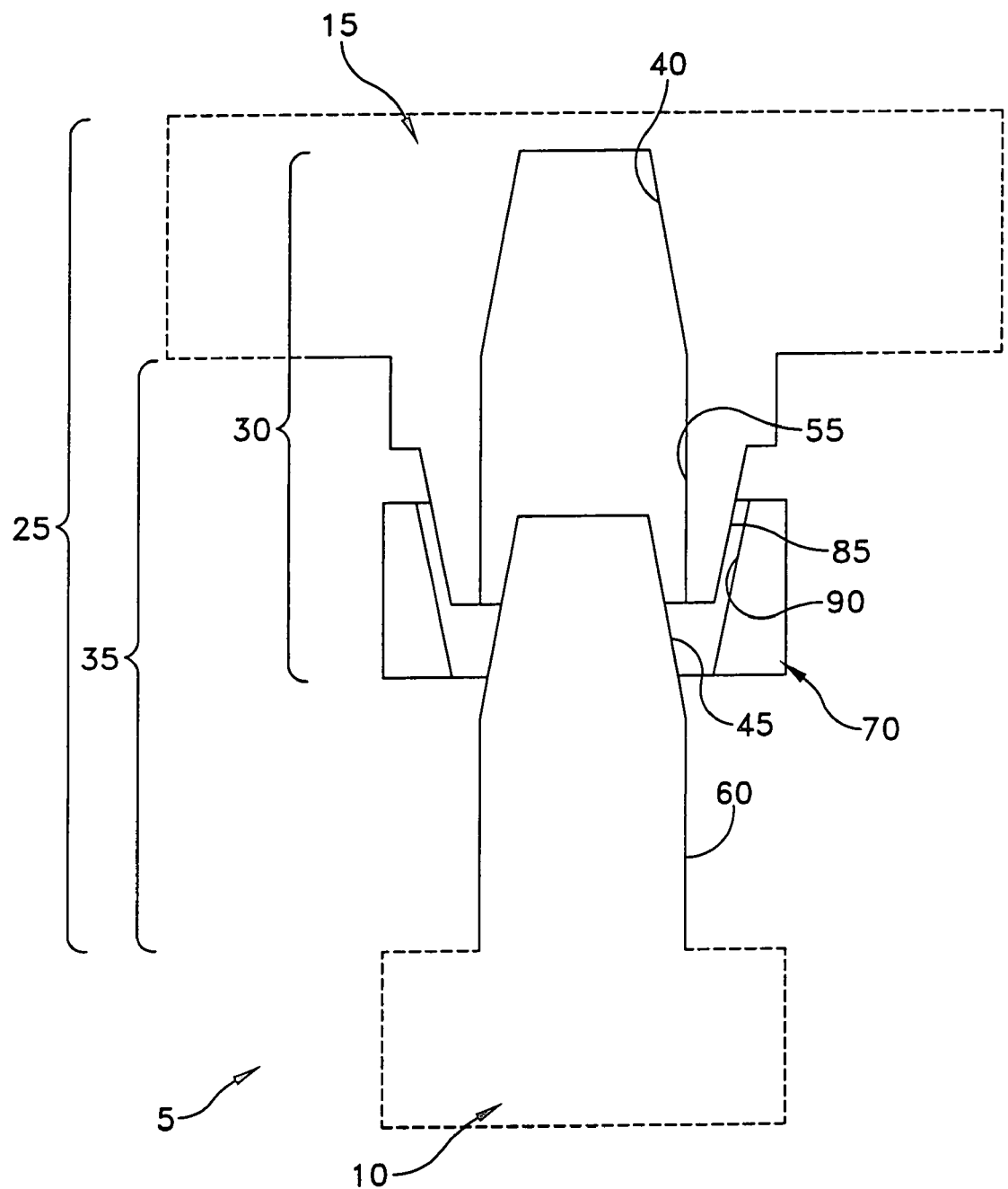
FIG. 5 is a schematic, exploded side view of another form of modular connection formed in accordance with the present invention.

Looking next at FIG. 5, there is shown yet another form of construction. Here, third element 70 is in the form of a ring and is used to drive second element 15 inward so as to effect the engaged-fit junction 35 between first concentric wall 55 and second concentric wall 60. Preferably this is effected by providing second element 15 with a taper surface 85 and third element 70 with a corresponding taper surface 90. In use, first element 10 and second element 15 are brought together so first taper 40 engage second taper 45 and so that first concentric wall 55 is adjacent to second concentric wall 60, and then third element 70 is moved toward second element 15 so that the engagement of taper surface 85 with taper surface 90 causes first concentric wall 55 to securely engage second concentric wall 60, whereby to actuate the engaged-fit junction 35.

It will be understood that many additional changes in the details, materials, steps and arrangement of parts, which have been herein described and illustrated in order to explain the nature of the invention, may be made by those skilled the art without departing from the principles and scope of the present invention.

What is claimed is:

1. A modular assembly for connecting together first, second and third elements to form an orthopedic component;
   wherein the first element comprises an elongated member having a circular aperture extending therethrough;
   the second element comprises a block member provided with a projection extending therefrom; and
   the third element comprises an elongated rod having a frusto-conically shaped projection at an end thereof;
   the assembly comprising:

a frusto-concially shaped entryway at a first end of the first element elongated member, said entryway forming a first taper and extending to the first element aperture;

a first portion of the second element projection having a second taper thereon, and a second portion of the second element projection having a frusto-conically shaped recess in a free end thereof;

wherein the second element projection second taper is engageable with the first taper at the first end of the aperture of the first element, and an external wall of the second element projection second portion is cylindrically shaped and is concentrically engageable with an inner wall of the first element aperture; and wherein the third element frusto-conically shaped end is engageable with the second element projection recess;

whereby to affix the second element to the first element and the third element to the second element to form the orthopedic component.

2. The modular assembly according to claim 1 wherein a taper junction is formed by the interaction of the first taper with the second taper.

3. The modular assembly according to claim 1 wherein the external wall of the second element projection second portion is deformable so as to be pressure locked against the inner wall of the first element aperture.

4. The modular assembly according to claim 3 wherein the external wall of the second element projection second portion is expandable so as to be pressure locked against the inner wall of the first element aperture.

5. The modular assembly according to claim 3 wherein an engaged-fit junction is formed by the interaction of the external wall of the second element projection second portion with the inner wall of the first element aperture.

* * * * *